(12) United States Patent
Mattson et al.

(10) Patent No.: US 6,461,040 B1
(45) Date of Patent: *Oct. 8, 2002

(54) APPARATUS AND METHOD TO CORRECT FOR POSITION ERRORS IN DIAGNOSTIC IMAGING

(75) Inventors: Rodney A. Mattson, Mentor; P. Gerhard Roos, Bainbridge; Donald E. Negrelli, Gates Mills, all of OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/378,448

(22) Filed: Aug. 20, 1999

Related U.S. Application Data

(63) Continuation-in-part of application No. 09/191,094, filed on Nov. 12, 1998, now Pat. No. 6,092,928.

(51) Int. Cl.$^7$ ................................................. A61B 6/08
(52) U.S. Cl. ...................................................... 378/205
(58) Field of Search ............................... 378/4, 15, 205

(56) References Cited

U.S. PATENT DOCUMENTS

| 4,803,712 A | * | 2/1989 | Kembo et al. | 378/34 |
| 4,934,832 A |   | 6/1990 | Strauss | 378/14 |

(List continued on next page.)

FOREIGN PATENT DOCUMENTS

| EP | 395 762 | 11/1990 |
| JP | 1-135332 | 5/1989 |

OTHER PUBLICATIONS

Analog Devices, Inc. Accelerometer Product, Oct. 1998 http://www.analogdevices.com/industry/items.

(List continued on next page.)

Primary Examiner—Robert H. Kim
Assistant Examiner—Allen C. Ho
(74) Attorney, Agent, or Firm—Fay, Sharpe, Fagan, Minnich & McKee, LLP

(57) ABSTRACT

An x-ray source (30, 80, 100) transmits a beam of x-rays through an examination region (E). A receiver (28, 82, 102), in an initial spatial orientation relative to the source (30, 80, 100), receives the beam and generates a view of image data indicative of the intensity of the beam received. A sensor, such as an accelerometer, detects motion in a selected portion of a mechanical structure (M) supporting the source (30, 80, 100) and the receiver (28, 82, 102). Upon detection of motion, the sensor generates a motion signal. In one embodiment, a first accelerometer (40, 90) is associated with the receiver (28, 82) and a second accelerometer (42, 88) is associated with the source (30, 80). A position calculator (58, 60) mathematically calculates a position of both the source and receiver based on the acceleration data generated by the accelerometers. An image reconstruction processor, (62) receives the relative position data, electronically corrects for any misalignment or change in beam travel distance, and reconstructs the views into a volumetric image representation. In another embodiment, a sensor (108) detects motion of a mechanical structure (M2) and provides a motion signal to a processor (110). The processor (110) compares the detected motion with a database loaded with an empirically determined vibration model. Based on this comparison, the processor (110) then generates a cancellation signal, which controls an electromechanical actuator (106) to impart an offsetting force or motion to the mechanical structure (M2).

21 Claims, 7 Drawing Sheets

U.S. PATENT DOCUMENTS

| | | | | |
|---|---|---|---|---|
| 5,109,397 | A | * | 4/1992 | Gordon et al. .............. 378/205 |
| 5,170,439 | A | | 12/1992 | Zeng |
| 5,266,863 | A | * | 11/1993 | Nonami et al. ............. 310/339 |
| 5,410,607 | A | * | 4/1995 | Mason et al. .............. 381/71.2 |
| 5,469,734 | A | * | 11/1995 | Schuman ..................... 73/105 |
| 5,553,113 | A | | 9/1996 | Weedon ..................... 378/98.5 |
| 5,592,523 | A | | 1/1997 | Tuy ............................. 378/19 |
| 5,625,660 | A | | 4/1997 | Tuy ............................. 378/15 |
| 5,757,951 | A | | 5/1998 | Tuy |
| 5,923,727 | A | * | 7/1999 | Navab ........................ 378/207 |
| 6,079,876 | A | * | 6/2000 | Schuetz ...................... 378/205 |
| 6,092,928 | A | * | 7/2000 | Mattson et al. ............. 378/205 |
| 6,097,784 | A | | 8/2000 | Tuy ................................ 378/4 |
| 6,256,364 | B1 | * | 7/2001 | Toth et al. ..................... 378/4 |

OTHER PUBLICATIONS

Summit Instruments, Inc. Accelerometer Product, Oct. 1998 http://www.summitinstruments/com/accel/index.htm.

Analog Devices, Inc. Accelerometer News Oct. 1998 http//www.analogdevices.com/publications/magazines/accel_news/issue6/4.htm.

"Dynamic Geometrical Calibration for 3–D Cerebral Angiography", N. Nauab et al., SPIE vol. 2708/361 (1996).

"Characterization of a C–arm Mounted XRII for 3D Image Reconstruction During Interventional Neuroradiology", R. Fahrig, et al., SPIE vol. 2708/351 (1996).

"Three–Dimensional Computed Tomographic Reconstruction Using a C–arm Mounted XRII: Correction of Image Intensifier Distortion", R. Fahrig, et al., Med. Phys., 24(7), 1097 (1997).

"Use of a C–arm System to Generate True Three–Dimensional Computed Rotational Angiograms: Preliminary In Vitro and In Vivo Results", R. Fahrig et all., Am. J. Neuroradiol 18:1507 (1997).

* cited by examiner

APPARATUS AND METHOD TO CORRECT FOR POSITION ERRORS IN DIAGNOSTIC IMAGING

RELATED APPLICATION

This application is a continuation-in-part of patent application Ser. No. 09/191,094, filed Nov. 12, 1998, U.S. Pat. No. 6,092,928.

BACKGROUND OF THE INVENTION

The present invention relates to the art of medical imaging. It finds particular application in conjunction with canceling or correcting for undesired movement especially mechanical movement in C-arm supports for generating three-dimensional computed tomography imaging data, more particularly fluoroscopic x-ray systems, and will be described with particular reference thereto. It is to be appreciated, however, that the invention is also applicable to other diagnostic imaging systems.

In some operating rooms, such as operating rooms for vascular catheter procedures, a projection x-ray imaging device is provided in association with the operating table. More specifically, an x-ray tube or generator and an x-ray detector are mounted on a C-arm which is positioned such that the area of interest or patient lies between the x-ray source and detector. The x-ray source and detector are rotatable and longitudinally displaceable as a unit to select a region and angle for projection imaging. Once the surgeon has positioned the x-ray source and detector in the proper position, the surgeon actuates the x-ray tube sending x-rays through the patient and onto the x-ray detector for a preselected exposure time. The x-rays received by the detector are converted into electronic, video image data representing a projection or shadow-graphic image. The projection or shadow-graphic image is displayed on a video monitor which is viewable by the physician.

In cardiac catheterization procedures, for example, images are generated to show the vasculature system and monitor the advance of the catheter through the blood vessels. More specifically, the surgeon advances the catheter into the patient, stops the surgical procedure, and initiates an x-ray imaging procedure. The x-rays are converted into electronic data and a projection image is displayed.

One of the drawbacks of these x-ray systems is that the resultant image is a projection or shadow-graphic image. That is, the 3-D vasculature system of the patient is projected into a single plane.

If 3-D diagnostic images are required, such images are often taken with a CT scanner or a magnetic resonance imaging device which is typically located in another part of the facility. Thus, any three-dimensional diagnostic images are commonly generated sometime before the surgical procedure starts. Even if a CT scanner is present in the surgical suite, the patient is still moved into the scanner. The transportation of the patient to the CT or MRI machine for further imaging often renders three-dimensional images impractical during many surgical procedures.

However, three-dimensional images obtained are valuable during surgical procedures. After generating a three-dimensional diagnostic image, a surgical procedure is commenced, such as a biopsy. From time to time during the procedure, additional projection diagnostic images are generated to monitor the advancement of the biopsy needle into the patient. The location of the needle can be mathematically predicted from the projection images and monitoring of the physical position of the needle or other instrument can be superimposed on the 3-D diagnostic images. As the needle moves, the superimposed images can be altered electronically to display the needle in the proper position. Various trajectory planning packages have been proposed which would enable the operator to plan the biopsy procedure in advance and electronically try various surgical paths through the three-dimensional electronic data.

Recently, there has been some interest in using relatively low power fluoroscopic systems to generate real time three-dimensional CT reconstructions. Such a technique, disclosed in U.S. Pat. No. 5,841,830 to Barni, et al. is assigned to the assignee of this invention. Barni suggests operating the x-ray tube of a CT scanner in a fluoroscopic mode. Unfortunately, the complete, encircling CT gantry can obstruct access to the surgical site or make that access inconvenient or uncomfortable for the physician.

Another solution disclosed by R. Fahrig, et al. in SPIE Volume 2708 entitled "Characterization Of A C-Arm Mounted XRII For 3-D Image Reconstruction During Interventional Neuro Radiology" recognizes that a C-arm would provide improved access to the surgical site. The Fahrig article also observes that the C-arm lacks sufficient rigidity to prevent the x-ray source and the detector plates from moving relative to each other, especially during a volume scan where the source and the detector are rotated about an area of interest. Relative motion misaligns the apparatus and causes image degradations. The Fahrig article describes a method wherein the motions and the deflections of the C-arm are premeasured or estimated in pilot scans. The deflections are assumed to remain the same for subsequent scans performed from the same starting point and within all other parameters. System calibration is performed by inserting a three-dimensional phantom containing metal beads or the like with known locations into the imaging field and performing a representative scan. Subsequent image analysis is used to determine positional errors, due to C-arm distortion and deflection. By comparing the detected position of the beads in each image with calculated ideal positions that would occur in the absence of any C-arm distortion, errors for each angular position of the C-arm are calculated. These errors, for each image scan, are stored in a long-term memory and applied to the data collected at corresponding positions of the C-arm, correcting for the calibration errors. Unfortunately, the Fahrig method requires that all volume imaging scans begin in exactly the same location and travel through the same arc. Moreover, any changes in the mechanical characteristics of the C-arm, such as bearing wear, changes in the source to image distance, drive speed, etc., will cause a deterioration in image quality due to the application of improper positional corrections.

The present invention provides a new and improved method and apparatus which overcomes the above-referenced problems and others.

SUMMARY OF THE INVENTION

In accordance with the present invention, a diagnostic imaging apparatus includes an x-ray source for transmitting a beam of x-rays through an examination region. An accelerometer is associated with the x-ray source such that a change in linear velocity of the source corresponds to an acceleration reading being registered by the accelerometer.

In accordance with a more limited aspect of the present invention, the diagnostic imaging apparatus includes a second accelerometer for measuring acceleration of the detector.

In accordance with a more limited aspect of the present invention, a position calculator mathematically calculates a position of both the source and the detector from data including signals provided by the accelerometers.

In accordance with a more limited aspect of the present invention, an image reconstruction processor is included to receive a plurality of image data views and for processing the views into a three-dimensional image representation using the calculated position data.

In accordance with a more limited aspect of the present invention, the diagnostic imaging apparatus also includes a collimator movably mounted to the x-ray source for restricting the cone beam of x-rays onto the detector. A misalignment processor receives the position data and controls a drive system mechanically linked to the collimator.

In accordance with another embodiment of the present invention, a radiographic imaging apparatus includes a penetrating radiation source and a radiation receiver. The source and receiver are held in position by a mechanical structure on opposite sides of an examination region. Moreover, the apparatus includes a sensor which detects motion in a selected portion of the mechanical structure and generates a signal in response to that motion. A processor receives the signal from the sensor and calculates a correction required to compensate for at least a portion of the motion detected. The processor then directs the correction calculated to be applied either as a physical correction to the structure or as imaging processing on the received radiation information.

In accordance with another aspect of the present invention, a process for diagnostic imaging includes positioning a radiation source and a receiver relative to an examination region. The process also includes sensing a motion affecting either the source, the receiver, or both and calculating a correction to compensate for the motion. Once the correction has been calculated it is applied either to physically cancel oscillations in a mechanical support before the source transmits a radiation beam; or as imaging processing on the received radiation information after the source transmits a radiation beam.

One advantage of the present invention resides in decreased bulk, or rigidity in the mechanical support needed to resist vibration or motion.

Another advantage of the present invention resides in the acquisition and display of more accurate volumetric images.

Another advantage of the present invention resides in computationally simpler and more efficient image signal manipulation.

Another advantage of the present invention resides in the ability to obtain volume scans from any starting and stopping position.

Another advantage of the present invention resides in the ability to provide dynamic corrections without relying on periodic calibration with three-dimensional phantoms.

Yet other benefits and advantages of the present invention will become apparent to those skilled in the art upon reading and understanding the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
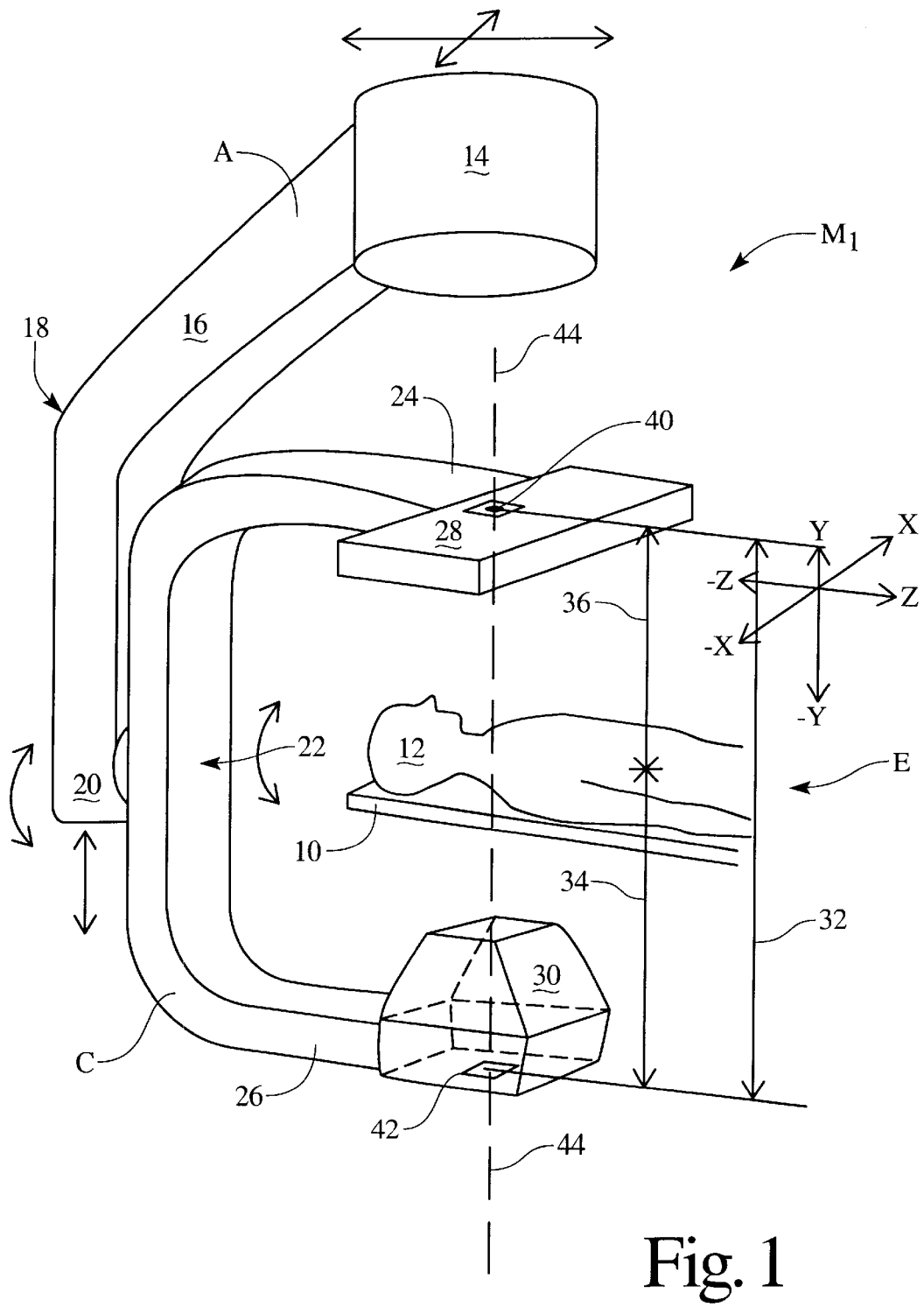
FIG. 1 is a diagrammatic illustration of an imaging system in accordance with the present invention.

With reference to FIG. 1, a mechanical structure $M_1$ configured as a C-arm C is supported by a rotational support assembly A, for rotation around an examination region E. The examination region E is describable by orthogonal axes X, Y, and Z. An x-ray transparent couch 10 is positioned such that a region of interest of a subject 12 is positioned in the examination region E. Vertical and horizontal drives (not shown) move the couch to facilitate positioning the region of interest at the center or other appropriate location in the examination region E. Alternatively, the rotational support assembly arm A moves in the X or Z direction.

The rotational support assembly A of the mechanical structure $M_1$ includes an overhead rotational mount or bearing 14 mounted to a ceiling or other overhead fixture for rotation about a vertical axis Y. In one preferred embodiment, the overhead rotational mount 14 is movably fixed to a track or other mechanism also allowing movement in the X and Z directions. An arm 16 extends away from the overhead mount 14 in the -Y direction through an elbow 18 to a lower rotational mount or bearing 20 with a horizontal axis of rotation.

A midpoint 22 of the C-arm C is rotatably attached to the lower bearing 20. The C-arm C defines two opposing parallel ends 24, 26, on either side of the examination region E. A receiver 28, such as a flat panel detector or the like for detecting x-ray radiation, is attached to the first end 24. The receiver 28 is preferably a solid state device, such as a grid of amorphous silicon detector elements, that generate x-ray intensity signals for each element of the grid. An x-ray source 30 is attached on the second end 26 of the C-arm. The C-arm C has sufficient strength to maintain the receiver 28 and x-ray source 30 in a substantially fixed spatial relationship. However, due to the mass of the x-ray tube and the arms, the ends 24, 26 deflect or move during positioning. On stopping the ends oscillate, but dampen back to the fixed position.

In order to obtain three-dimensional images, the source 30 and the receiver 28 are rotated in a plane perpendicular to the axis of the lower bearing 20 i.e. in the X-Y plane. Elongated volume scans can also be achieved by adding relative motion along the Z axis. Accurate three-dimensional reconstruction requires an accurate knowledge of the x-ray path through the examination region E and a distance 32 between the receiver 28 and the source 30, more particularly a distance 34 between the source 30 and the region of interest and a distance 36 between the region of interest and the receiver 28.

In a preferred embodiment, the receiver 28 and the x-ray source 30 both include three-dimensional Micro-Electro- Mechanical (MEMS) accelerometers 40, 42. MEMS accelerometers are known and commercially manufactured. The accelerometers 40, 42 are positioned ideally along a central axis 44 passing through a geometric center of the receiver 28 and a center of a focal spot on the source 30 for mathematical convenience. However, it is appreciated that the accelerometers could also be located at other known positions within the housings of the receiver and the source offset from the central axis. Moreover, in addition to MEMS devices, use of other accelerometers or accurate position sensing devices is also envisioned by the present invention such as gyroscopes, inertial sensors, and the like.

Figure 2:
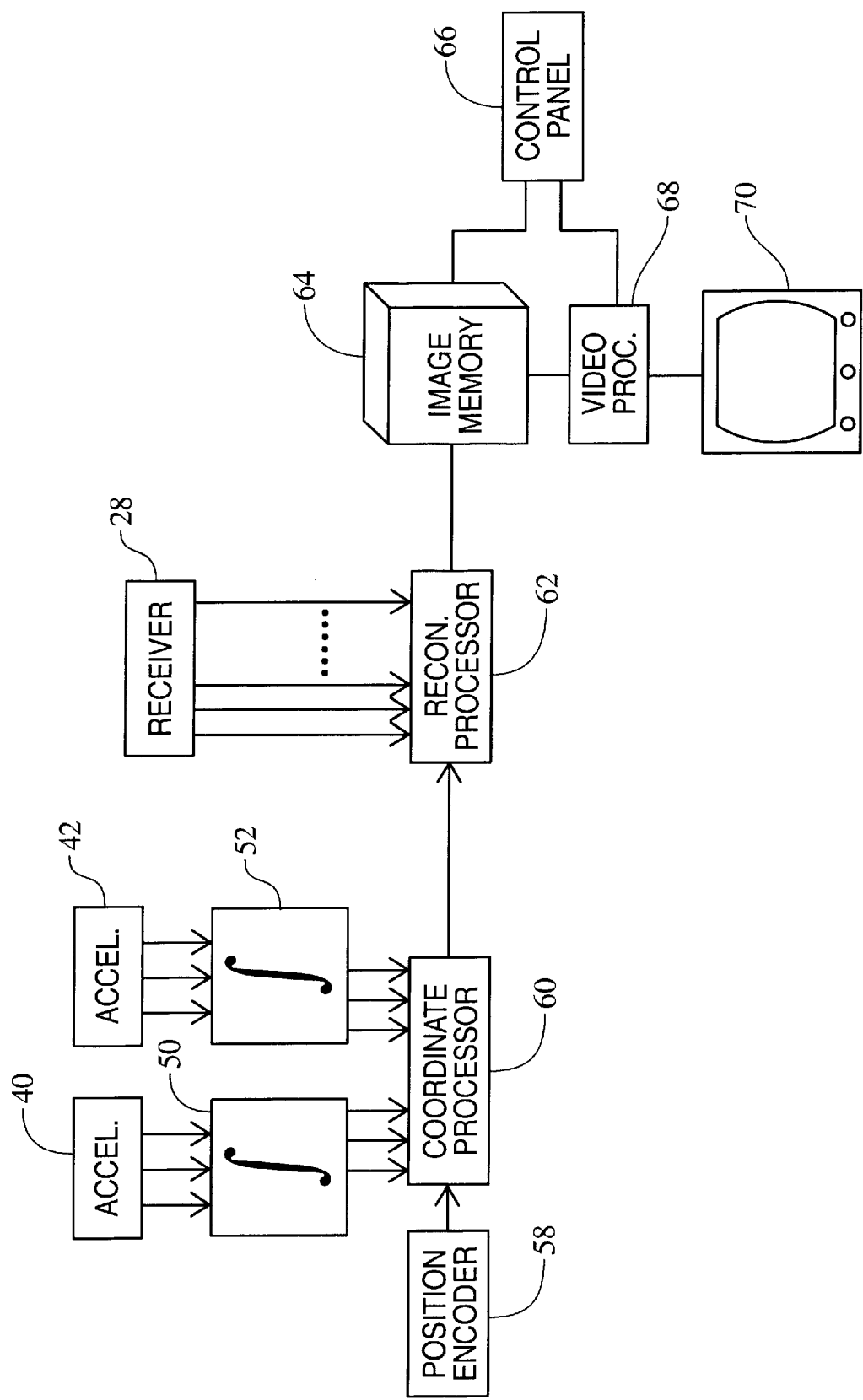
FIG. 2 is a block diagram of a signal processor in accordance with the present invention.

Now referring to FIG. 2, the accelerometers 40, 42 each generate electronic acceleration data indicative of acceleration along volumetric coordinates. Integrators 50, 52 perform a double integral on the acceleration data along each of the coordinates to determine cumulative displacement relative to each coordinate from an initial starting point. At each data sampling point, the integrators 50, 52 are sampled to provide the deflection error corresponding to each view of image data. It is to be appreciated that, the accelerometers and integrators can provide the displacement data in rectangular coordinates, polar coordinates, or the like. Further, depending on the motion direction and the construction of the C-arm, one can choose to determine the displacement along only one or two coordinates.

A position encoder 58 determines the initial starting position preferably in the same coordinates. A coordinate processor 60 calculates the orientation of the central axis 44, the source and receiver positions for each sampling position from the starting position and the cumulative displacements. If the integrators are zeroed at the starting position, actual position can be calculated by simply adding the cumulative displacement to the starting position. Optionally, the coordinate processor 60 uses the output of the encoder 58 to determine an offset error, skew error or the like at each view sampling position. Either way, the output indicates the actual trajectory of each ray of each view through the examination region.

Figure 3:
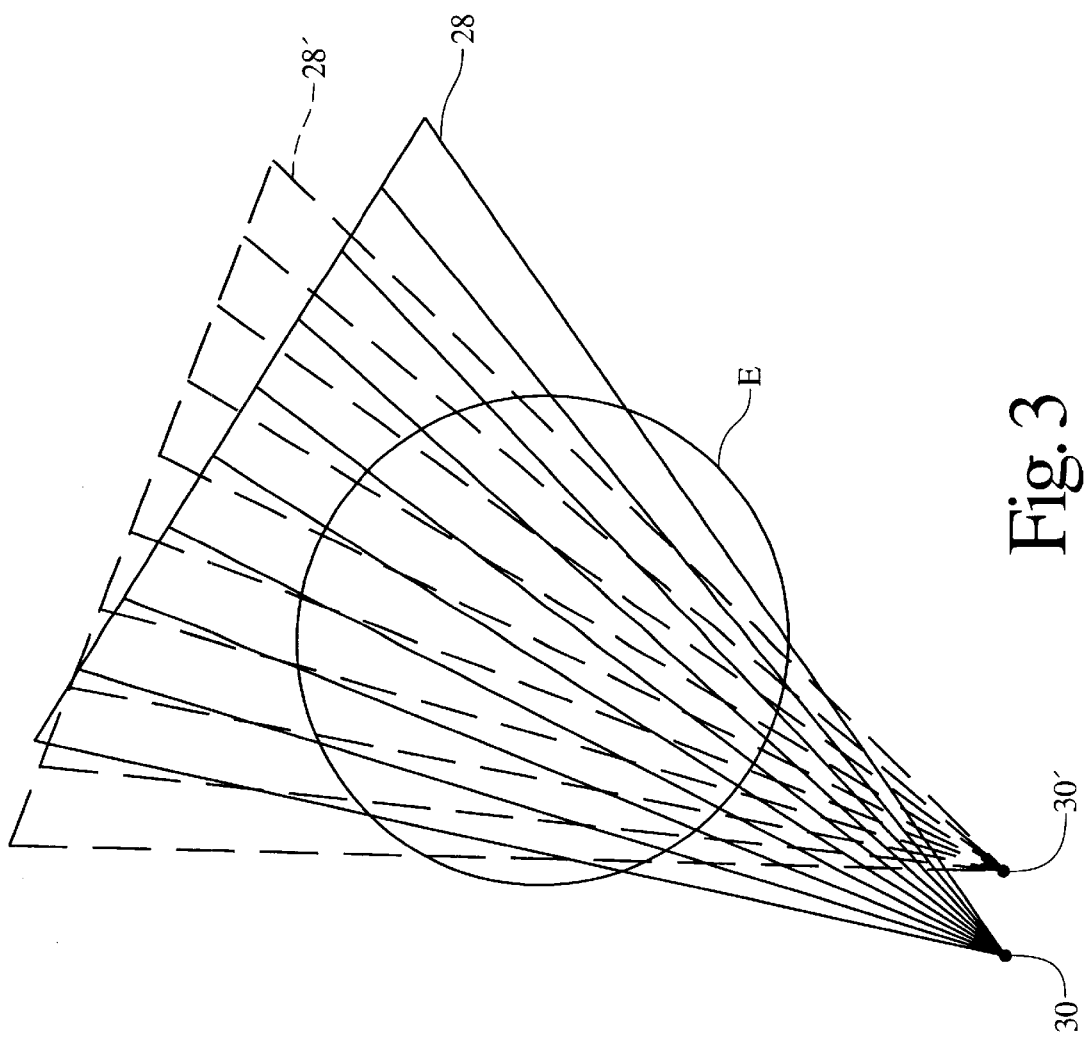
FIG. 3 is a depiction of error induced by deflection.

An image reconstruction processor 62 applies known reconstruction algorithms for cone beam data to each sampled view. Each view is convolved or otherwise processed and then back projected into a volume image memory 64. Conventional reconstruction algorithms assume that each view is collected at the selected sampling position and represents radiation attenuation along rays (shown in solid) between the source 30 and the receiver 28 as shown in FIG. 3. Rather than projecting the data along the expected rays, the reconstruction processor 62 uses the actual position of the source 30' and the receiver 28' to project the data along the actual rays (shown in phantom). Depending on the exact algorithm chosen, the ray trajectories are corrected by rotational offsets, angular offsets, magnification correction, redefining the ray trajectories, and the like.

The volume image is reconstructed, built, and stored as voxels in the volume memory 64. An operator control panel 66 enables the operator to select various image representations, such as slice images, slab images, volume images, and the like to be displayed. A video processor 68 samples the appropriate voxels in the volume memory and converts the data to approximate form for display on a monitor 70.

Figure 4:
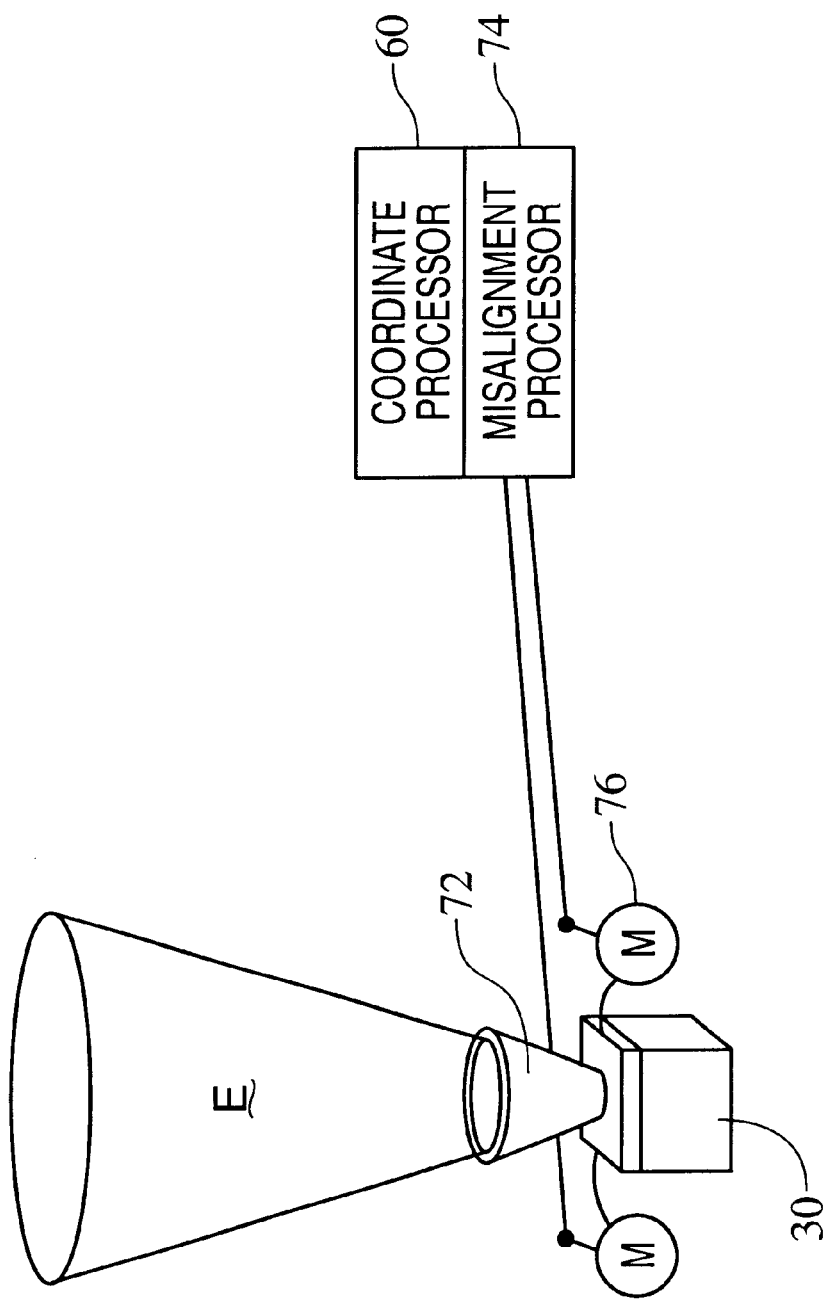
FIG. 4 is a diagrammatic illustration of collimator adjustment to correct for induced errors.

Referring to FIG. 4, the x-ray source 30 includes a collimator 72 which projects the x-ray beam through the examination region E onto the x-ray receiver 28 with little or no overscan. When the receiver and source deflect by different amounts, the source and receiver may become misaligned. To correct the misalignment, a misalignment processor 74 calculates a misalignment correction and controls a servomotor 76 to reposition the collimator 72 thus realigning the x-ray beam onto the receiver.

The use of three-axis accelerometers on the position sensitive imaging components can result in an overall reduction in system cost. Less massive structures can be used because precise positional information is readily available even when the structures deflect. The invention thus has the advantage that a highly versatile positioning structure, such as a fluoroscopic C-arm or other devices that are subject to mechanical distortion, can be used for a high precision image procedures, such as volume image reconstructions. Moreover, accelerometer use can also result in increased system availability. Time consuming calibration and re-calibration runs to correct for wear and aging are no longer required since position correcting data is developed on-the-fly during the diagnostic imaging procedure.

Figure 5:
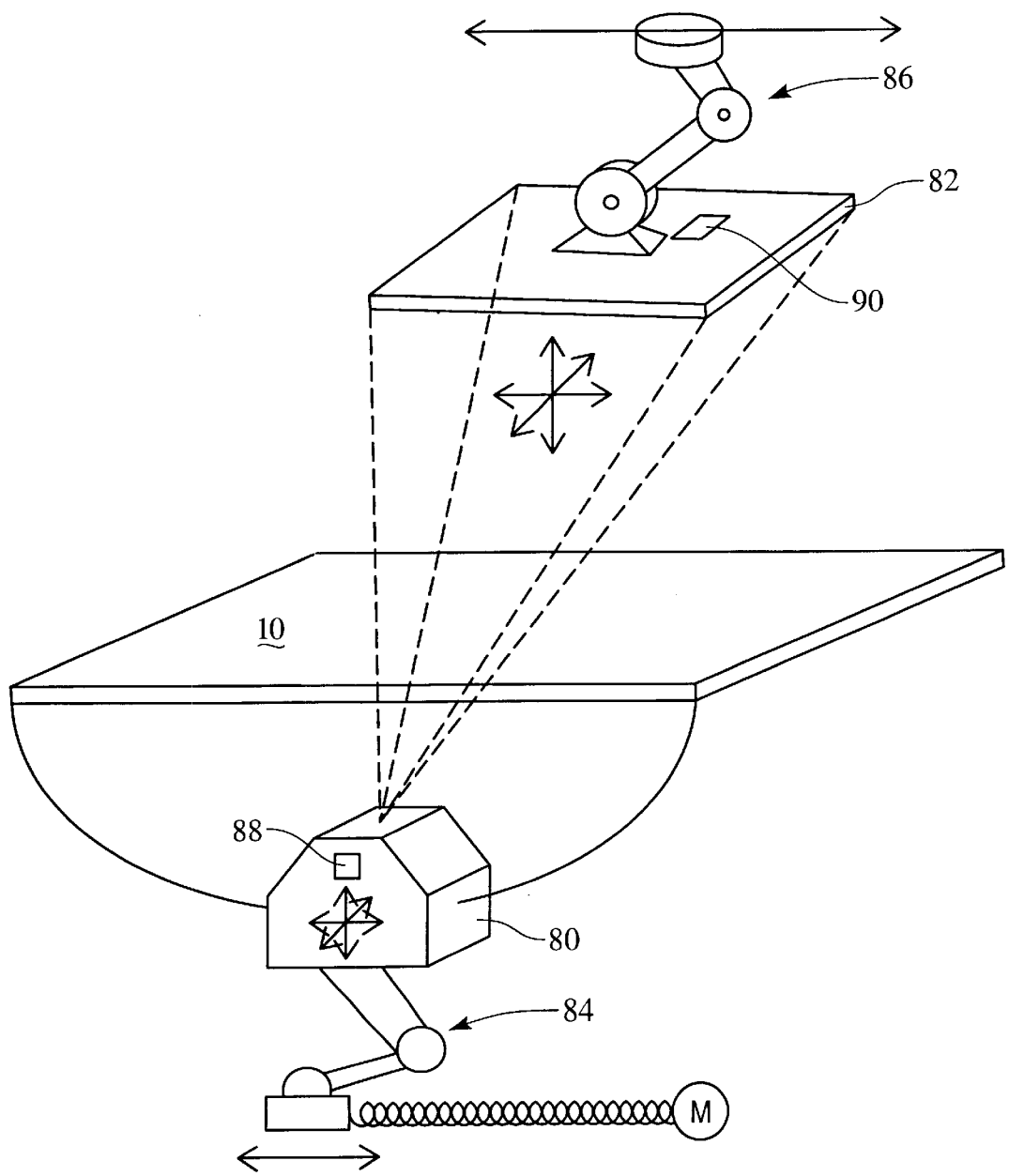
FIG. 5 shows a diagrammatic illustration of an alternate embodiment of the present invention.

Now referring to FIG. 5, an independent movable radiation source 80 and receiver 82 can be utilized. In other words, the source and the receiver are not connected to a common frame. In a preferred embodiment, the source 80 is mounted to the floor by a mechanical support structure 84 capable of inducing motion. The receiver is attached to a similar three degrees of movement structure 86 suspended from the ceiling. MEMS accelerometers 88, 90, as discussed above with reference to FIG. 1, are mounted to the source and the receiver. Preferably, a fixed repeatable docking position is defined as a reference position for zeroing the accelerometers.

Figure 7:
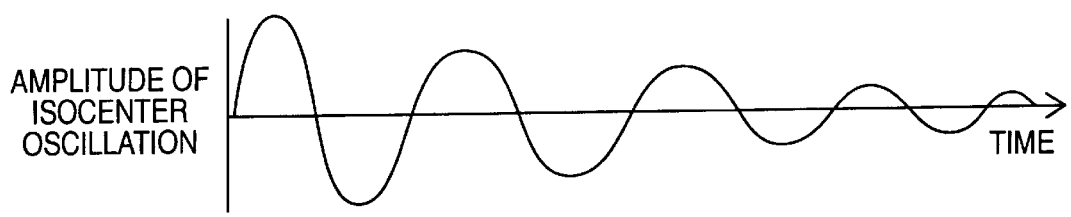
FIG. 7 is an oscillation curve showing motion of an isocenter over time.
Figure 6:
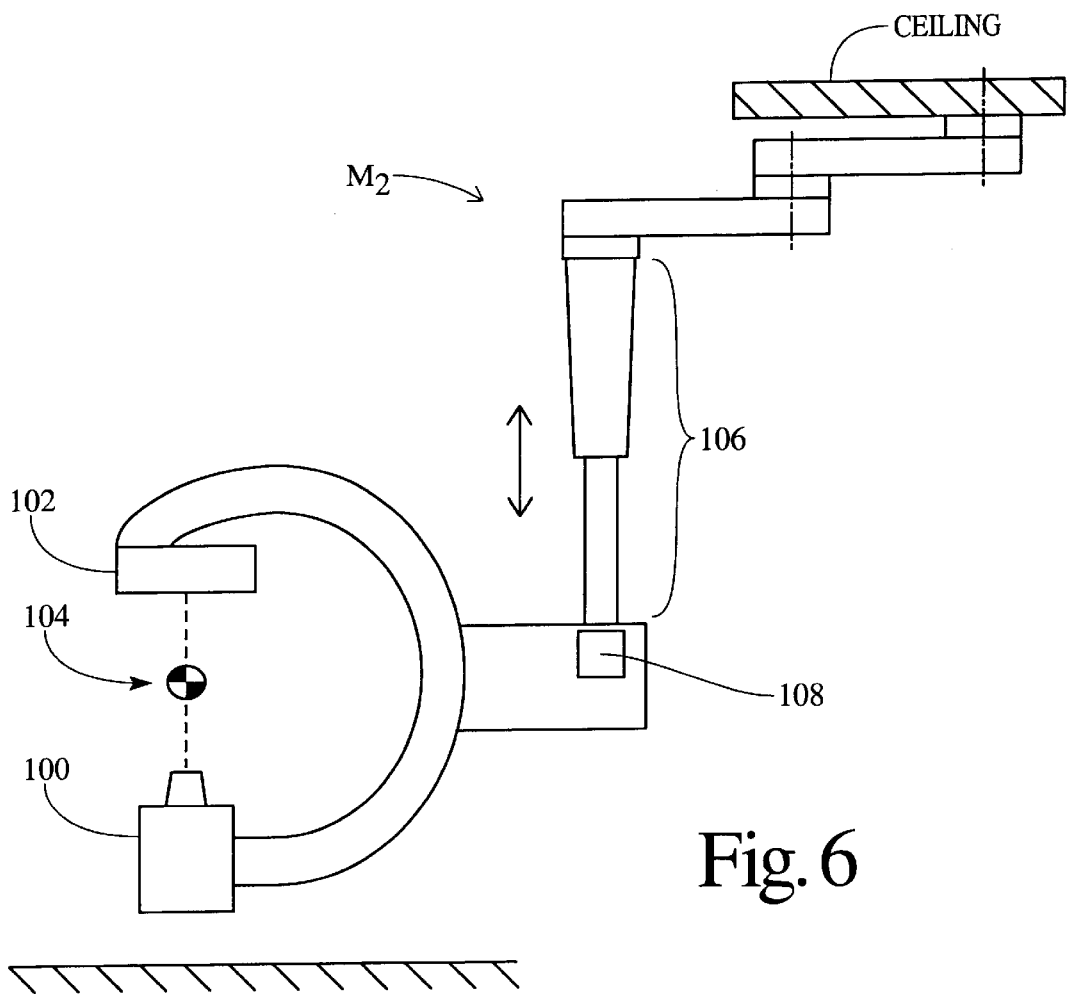
FIG. 6 is a diagrammatic illustration of an imaging system suitable to practice an alternate embodiment of the present invention.

Referring now to FIG. 6, an imaging apparatus includes a mechanical structure $M_2$ supporting a radiation source 100 and a radiation receiver 102 surrounding an isocenter 104. A mechanical actuator 106 is preferably provided to vary the height of the isocenter 104. Those skilled in the art will recognize that activating the actuator 106 will induce an oscillatory motion in the mechanical structure $M_2$, particularly in the cantilevered arms and pivots that support the mechanical actuator from the ceiling. Motion of the isocenter 104 due to the oscillation is best appreciated by reference to FIG. 7.

Figure 8:
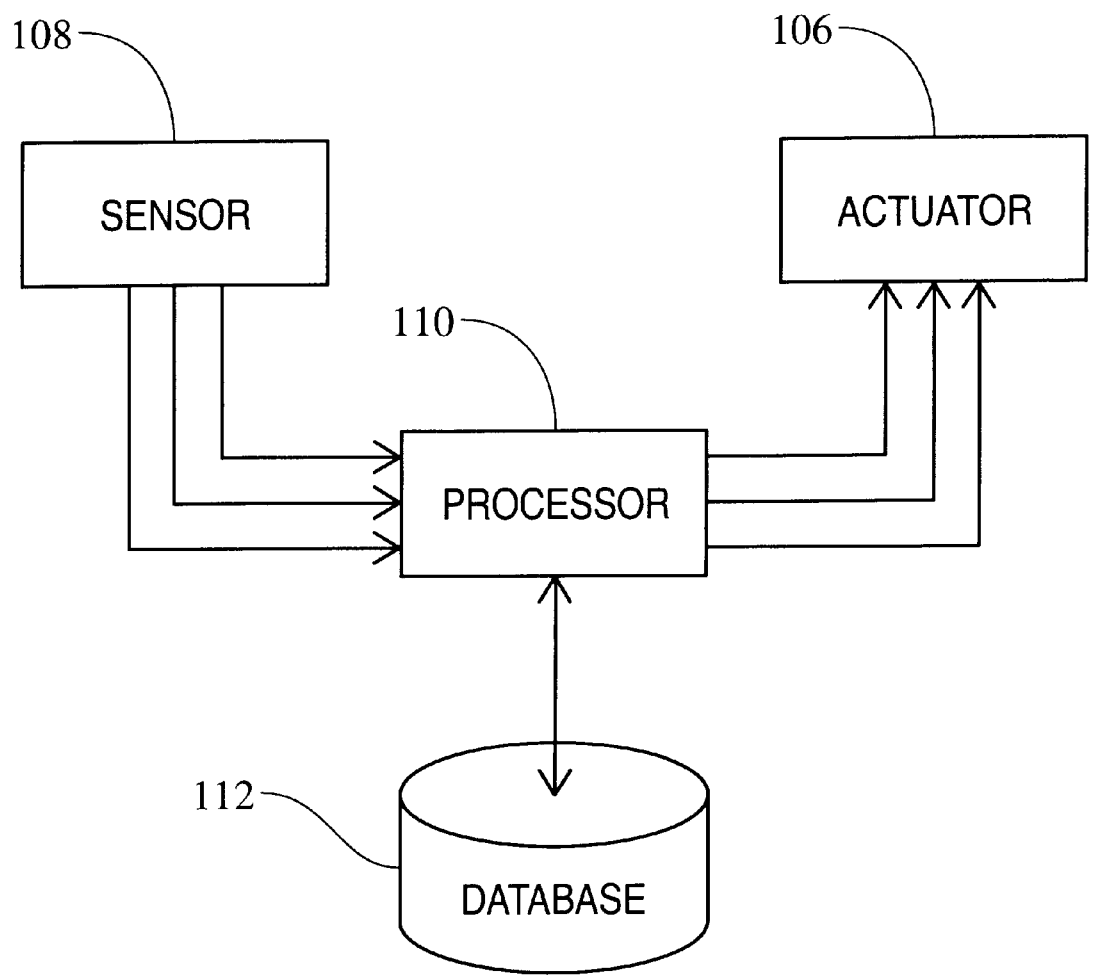
FIG. 8 is a block diagram of signal processing system for practicing the present invention.

Referring back to FIG. 6, the apparatus also includes a sensor 108 for detecting motion, especially vibration, in the mechanical structure $M_2$. Sensor 108 additionally generates a signal indicative of the motion sensed for processing by processor 110 (FIG. 8). In one preferred embodiment the sensor 108 is configured as an accelerometer which detects motion or vibration in at least one axis, particularly the vertical movement. Alternately, the sensor includes a strain gauge which senses and signals deflection.

Referring now to FIG. 8, the processor 110 preferably compares the sensed or detected oscillation against a database 112 of previously calibrated and stored data. From the data, the processor 110 generates a cancellation signal, preferably an equal amplitude, out of phase oscillation. The processor 110 then drives the actuator 106 to impart the cancellation movement to the mechanical structure $M_2$. More specifically to the preferred embodiment, as the sensor senses that the C-arm assembly is starting to move downward, the cancellation signal causes the actuator 106 to contract pulling the C-arm assembly up. Conversely, when the C-arm assembly starts to move upward, the actuator 106 extends creating a downward motion. By matching the magnitudes of the extensions and contractions of the actuator to the magnitude of the vibrations, the C-arm assembly is held stationary as the upper arms oscillate.

Those skilled in the art will recognize that actuator 106 can comprise existing actuators used to position the imaging apparatus. Alternately, piezo-electric or other rapidly responding actuators can be combined with the mechanical actuator. For example, the rapidly responding actuator can be mounted between the mechanical actuator 106 and the C-arm assembly. Also, while the description above illustrates sensing and correcting oscillations in only one plane, the present invention envisions detection and cancellation of oscillatory motion in all three axes. It will be noted that as the ceiling arms oscillate, the C-arm assembly tends to move not only downward (or upward) but also tip or lean downward (or cant upward). The rapidly responding actuators are advantageously positioned fore and aft the interconnection between the actuator 106 and the C-arm assembly to counteract the cyclic tipping.

Alternately, an additional motion sensor(s) is mounted to the ceiling arms to monitor their motion directly. As yet another alternative, motion sensors are mounted to the detector 102 and the x-ray tube 100. Rapidly responding actuators are positioned at the detector and the x-ray tube to counteract any vibratory or other degrading motion that reaches the detector and the x-ray tube.

The invention has been described with reference to the preferred embodiments. Potential modifications and alterations will occur to others upon a reading and understanding of the specification. For example, accelerometers could also be employed in other medical imaging applications such as fluoroscopy, angiography, ultrasound, etc. It is our intention to include all such modifications and alterations insofar as they come within the scope of the appended claims, or the equivalents thereof.

Having thus described the preferred embodiment, the invention is now claimed to be:

1. A radiographic imaging apparatus including a penetrating radiation source which generates a beam of radiation, a radiation receiver which receives the beam of radiation, and a mechanical structure including a building mounted structure and a movable structure movably mounted to the building mounted structure for supporting the radiation source and the receiver on opposite sides of an examination region, the apparatus further comprising:

a sensor which detects cumulative motion in both the building mounted structure and the movable structure and generates a motion signal indicative of said detected motion;

a processor configured to receive the generated motion signal from the sensor and generating a correction signal to compensate for the detected motion; and, an electromechanical actuator which converts the correction signal into offsetting mechanical motion that is applied to the mechanical structure to compensate for the detector motion.

2. The radiographic imaging apparatus as set forth in claim 1, wherein the sensor includes a strain gauge.

3. The radiographic imaging apparatus as set forth in claim 1, wherein said e lectromechanical actuator applies a motion to the mechanical structure that is equal and opposite to the detected motion.

4. The radiographic imaging apparatus as set forth in claim 3, wherein said actuator includes a piezoelectric actuator.

5. The radiographic imaging apparatus as set forth in claim 1, wherein said electromechanical actuator applies destructive interference to said motion detected.

6. A radiographic imaging apparatus including a penetrating radiation source which generates a beam of radiation, a radiation receiver which receives the beam of radiation, and a mechanical structure for supporting the radiation source and the receiver on opposite sides of an examination region, the apparatus further comprising:

an accelerometer which measures acceleration in the mechanical structure in at least one dimension and generates a motion signal indicative of said detected motion;

a processor configured to receive the generated motion signal from the accelerometer and generating a correction signal to compensate for the detected motion; and, an electromechanical actuator which converts the correction signal into offsetting mechanical motion that is applied to the mechanical structure to compensate for the detected motion.

7. A radiographic imaging apparatus including a penetrating radiation source which generates a beam of radiation, a radiation receiver which receives the beam of radiation, a main gantry, and a movable gantry movably mounted to the main gantry for movably supporting the radiation source and the receiver on opposite sides of an examination region, the apparatus further comprising:

sensors which detect cumulative motion of the main and movable gantries at the radiation source and the radiation receiver and which generate motion signals indicative of said detected motions;

a processor configured to receive the generated motion signals from the sensors to generate correction signals to compensate for the detected motions, and to correlate the motion signals and the correction signals to vibrations.

8. A radiographic imaging apparatus including a penetrating radiation source which generates a beam of radiation, a radiation receiver which receives the beam of radiation, and a mechanical structure for supporting the radiation source and the receiver on opposite sides of an examination region, the apparatus further comprising:

a first accelerometer associated with the radiation source such that a change in acceleration of the source corresponds to a change in acceleration of the accelerometer, the first accelerometer generating a first detected motion signal indicative of acceleration in at least one dimension;

a second accelerometer for measuring acceleration of the radiation receiver in at least one dimension and generating a second detected motion signal indicative of the measured acceleration of the radiation receiver;

a processor configured to receive the generated motion signals from the accelerometers and generating a correction signal to compensate for the detected motion.

9. The radiographic imaging apparatus as set forth in claim 8, wherein said processor includes a position calculator for mathematically calculating:

a position of the radiation source from data including the first detected motion signal; and, a position of the receiver from data including the second detected motion signal.

10. The radiographic imaging apparatus as set forth in claim 9, further including an image reconstruction processor for:

receiving a plurality of image data views from the receiver at selected positions;

receiving the first and second detected motion signals; and, processing said image data views into a three-dimensional image representation corrected for the detected motion signals.

11. A radiographic imaging apparatus including a penetrating radiation source which generates a beam of radiation, a radiation receiver which receives the beam of radiation, a main gantry, and a movable gantry movably mounted to the main gantry for supporting the radiation source and the receiver on opposite sides of an examination region, the apparatus further comprising:

a sensor which detects motion between portions of the movable gantry and generates motion signals indicative of said detected motion;

an actuator which applies a motion to at least the movable gantry and generates motion signals indicative of said detected motion;

a processor for receiving a plurality of image data views from the radiation receiver at each of a plurality of positions and for processing the image data views into a three dimensional image representation corrected for the compensated detected motion.

12. A radiographic apparatus including:

a radiation source mounted at a first position for transmitting a beam through an examination region;

a detector mounted at a second position for receiving the beam and generating signals indicative of intensity of the beam; and, a first accelerometer mounted for detecting a motion and generating a first motion signal of the radiation source relative to at least one dimension as the radiation source is moved.

13. The radiographic apparatus of claim 12 further including:

a second sensor mounted for detecting a motion and generating a second motion signal of the radiation detector relative to at least one dimension as the radiation detector is moved;

a converter for mathematically calculating:
  a calculated position of the source from data including the first motion signal, and
  a calculated position of the detector from data including the second motion signal; and, an image reconstruction processor for generating an image representation from a plurality of the detector signals and the calculated positions of the source and the detector.

14. A radiographic apparatus including:

a radiation source mounted at a first position for transmitting a beam through an examination region;

a detector mounted at a second position for receiving the beam and generating signals indicative of intensity of the beam;

sensors mounted for detecting a relative motion and generating a motion signal indicative of movement of the radiation source and the radiation detector relative to each other and relative to the examination region;

a processor configured to receive the motion signals from the sensors and generate a correction signal to compensate for the detected motion; and, an electromechanical actuator which converts the correction signal into offsetting mechanical motion that is applied to the apparatus to compensate for the detected motion.

15. A process for diagnostic imaging comprising:

transmitting a beam of radiation from a radiation source through an examination region to a receiver;

positioning said radiation source and said receiver relative to said examination region;

sensing motion of at least one of said source and said receiver;

determining a position of at least one of said source and said receiver from said sensed motion;

calculating a correction to compensate for at least a portion of said motion sensed.

16. The process as set forth in claim 15 further including:

adjusting data sampled from said receiver in accordance with the calculated correction.

17. A process for diagnostic imaging comprising:

transmitting a beam of radiation from a radiation source through an examination region to a receiver;

positioning said radiation source and said receiver relative to said examination region;

sensing motion of at least one of said source and said receiver;

determining a misalignment between said source and said receiver from the sensed motion; and redirecting said beam of radiation.

18. A radiographic imaging method in which radiation is transmitted from a radiation source through an examination region and received and converted into electronic image data by a radiation receiver, the method further comprising:

detecting a vibration in a selected portion of a mechanical structure for the source and the receiver; and based on stored vibration modeling data, generating a correction signal for canceling said detected vibration.

19. A radiographic imaging method in which radiation is transmitted from a radiation source through an examination region to a radiation receiver which converts the received radiation into electronic image data, the radiation source and receiver being supported on a common support structure which is movably mounted to a main support structure, the method further comprising:

detecting a vibration of at least one of the source and the receiver attributable to cumulative vibration of both the common and main support structures;

generating a correction signal for canceling said detected vibration; and, applying a mechanical force to the common support structure to offset the detected vibration.

20. A radiographic imaging method in which radiation is transmitted from a radiation source through an examination region and received and converted into electronic image data by a radiation receiver, the method further comprising:

monitoring acceleration of at least one of said source and said receiver; and correcting for the monitored acceleration.

21. The method as set forth in claim 20, where the correcting step includes:

deriving a position from the monitored acceleration; and, based on said derived position, reconstructing a series of views of image data, indicative of an intensity of radiation received by said receiver into an electronic image representation.

* * * * *